United States Patent
Krill et al.

(10) Patent No.: US 7,423,173 B2
(45) Date of Patent: Sep. 9, 2008

(54) METHOD FOR PRODUCING ALPHA-HYDROXYCARBOXYLIC ACIDS AND THE ESTERS THEREOF

(75) Inventors: Steffen Krill, Speyer (DE); Friedel Schultheis, Hasselroth (DE); Udo Gropp, Heppenheim (DE); Matthias Groemping, Kenner, LA (US)

(73) Assignee: Roehm GmbH & Co. KG, Darmstadt (DE)

( * ) Notice: Subject to any disclaimer, the term of this patent is extended or adjusted under 35 U.S.C. 154(b) by 73 days.

(21) Appl. No.: 10/589,123

(22) PCT Filed: Jan. 21, 2005

(86) PCT No.: PCT/EP2005/000578

§ 371 (c)(1),
(2), (4) Date: Aug. 11, 2006

(87) PCT Pub. No.: WO2005/077878

PCT Pub. Date: Aug. 25, 2005

(65) Prior Publication Data

US 2007/0173664 A1    Jul. 26, 2007

(30) Foreign Application Priority Data

Feb. 11, 2004    (DE) .................. 10 2004 006 826

(51) Int. Cl.
*C07C 51/06* (2006.01)
*C07C 59/01* (2006.01)
*C07C 57/04* (2006.01)
*C07C 51/37* (2006.01)

(52) U.S. Cl. ..................................... 562/526; 562/599
(58) Field of Classification Search ...................... None
See application file for complete search history.

(56) References Cited

U.S. PATENT DOCUMENTS

| 2,229,897 A | 1/1941 | Migrdichian |
| 2006/0211880 A1 | 9/2006 | Ackerman et al. |
| 2007/0173664 A1 | 7/2007 | Krill et al. |

FOREIGN PATENT DOCUMENTS

| DE | 1 768 253 | 10/1971 |
| EP | 0 487 853 | 6/1992 |
| JP | 57 131736 | 8/1982 |

OTHER PUBLICATIONS

U.S. Appl. No. 11/915,042, filed Nov. 20, 2007, Ackermann et al.
U.S. Appl. No. 11/914,493, filed Nov. 15, 2007, Ackermann et al.
U.S. Appl. No. 11/995,206, filed Jan. 10, 2008, Sarcinelli et al.
U.S. Appl. No. 60/893,788, filed Mar. 8, 2007, May et al.

*Primary Examiner*—Yvonne Eyler
*Assistant Examiner*—Yevegeny Valenrod
(74) *Attorney, Agent, or Firm*—Oblon, Spivak, McClelland, Maier & Neustadt, P.C.

(57) ABSTRACT

The invention relates to a process for the selective, economically viable preparation of methacrylic acid and methacrylic esters starting from acetone cyanohydrin, wherein, in a first step, 2-hydroxy-2-methylpropionic acid is prepared by reacting acetone cyanohydrin with sulphuric acid in the presence of water and a suitable polar solvent and is isolated and methacrylic acid is subsequently prepared by β-elimination of water starting from 2-hydroxy-2-methylpropionic acid.

18 Claims, 1 Drawing Sheet

METHOD FOR PRODUCING ALPHA-HYDROXYCARBOXYLIC ACIDS AND THE ESTERS THEREOF

Figure 1:
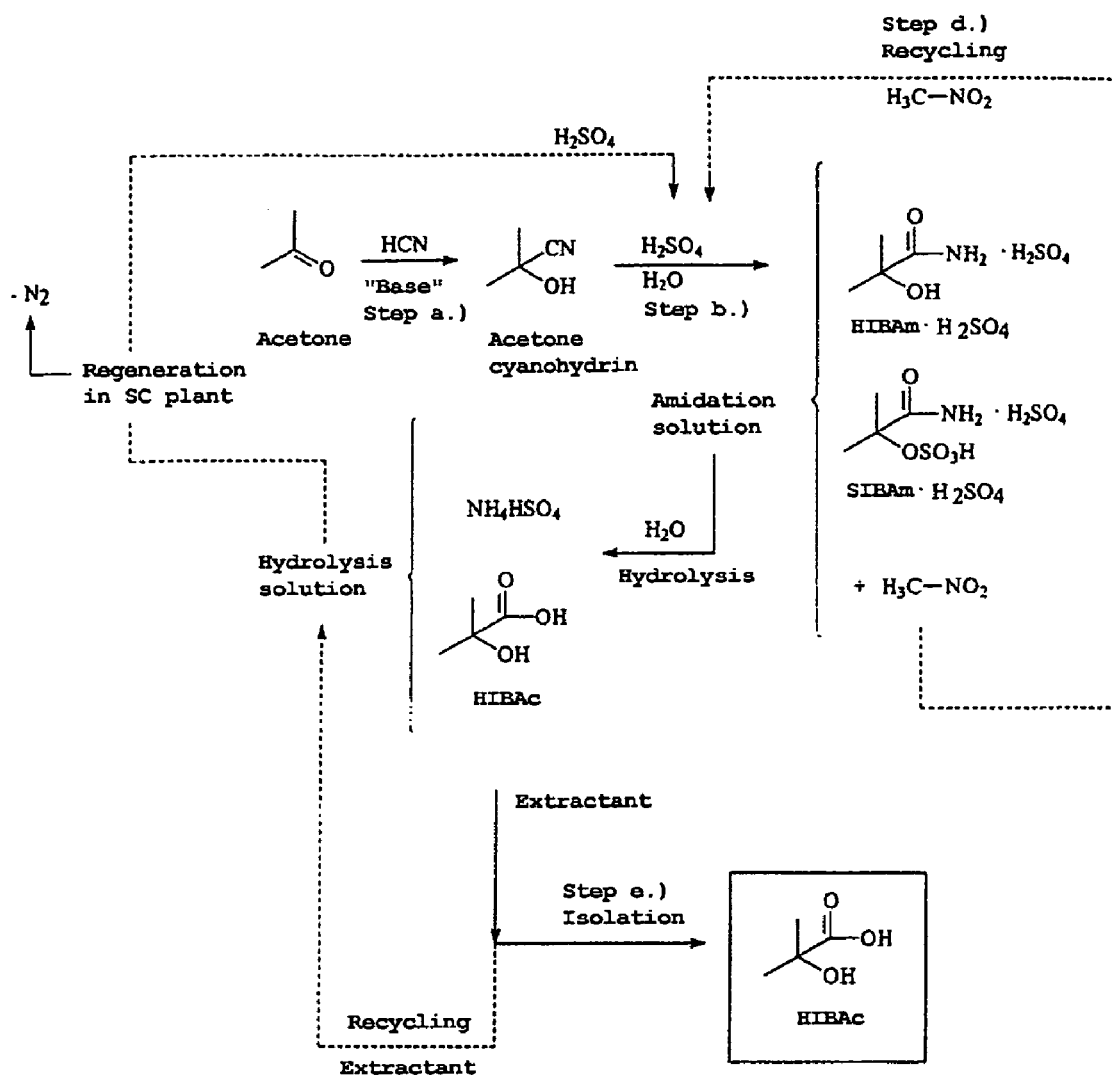

The present invention relates to a process for the selective, economically viable preparation of alpha-hydroxy carboxylic acids and esters thereof and dehydration products derived therefrom, especially methacrylic acid and methacrylic esters, starting from cyanohydrins.

Methacrylic acid and methacrylic esters find their main field of use in the preparation of polymers and copolymers with other polymerizable compounds. Methacrylic esters, for example methyl methacrylate, is additionally an important building block for diverse special esters based on methacrylic acid which are prepared by transesterification with the appropriate alcohol.

Methyl methacrylate (MMA) and methacrylic acid are today prepared predominantly starting from hydrocyanic acid and acetone via the acetone cyanohydrin (ACH) which is formed as a central intermediate.

Further processes which use a raw material basis other than ACH are described in the relevant patent literature and in the meantime have been realized on the production scale. In this connection, C-4 based raw materials such as isobutylene or tert-butanol are used today as reactants which are converted to the desired methacrylic acid derivatives via a plurality of process stages.

An additional subject of intensive investigation has been the use of propene as a base raw material, in which case methacrylic acid is obtained in moderate yields via the stages of hydrocarbonylation (to isobutyric acid) and dehydrogenating oxidation.

It is known that propanal or propionic acid which are obtainable in industrial processes starting from ethylene and C-1 building blocks such as carbon monoxide can be used as the base raw material. In these processes, an aldolizing reaction with formaldehyde converts the β-hydroxycarbonyl compound formed in situ under dehydration to the corresponding α,β-unsaturated compounds. An overview of the common processes for preparing methacrylic acid and esters thereof can be found in the literature such as Weissermel, Arpe "Industrielle organische Chemie" [Industrial organic chemistry], VCH, Weinheim 1994, 4th edition, p. 305 ff or Kirk Othmer "Encyclopedia of Chemical Technology", 3rd edition, Vol. 15, page 357.

It is commonly known that industrial processes based on ACH and using highly concentrated sulphuric acid (about 100% by weight. $H_2SO_4$) in the first step of the reaction, known as the amidation, are carried out at temperatures between 80° C. and about 110° C.

Representative of such a process is, for example, U.S. Pat. No. 4,529,816 in which the ACH amidation is carried out at temperatures of around 100° C. with a molar ratio of ACH:$H_2SO_4$ of from about 1:1.5 to 1:1.8. Relevant process steps for this process are: a) amidation; b) conversion; and c) esterification.

In the amidation, the main products of the reaction which are obtained are SIBAm=sulphoxy-alpha-hydroxyisobutyramide hydrogensulphate and MAA·$H_2SO_4$=methacrylamide-hydrogensulphate as a solution in excess sulphuric acid. In addition, HIBAm·$H_2SO_4$=alpha-hydroxyisobutryamide hydrogensulphate is also obtained in a typical amidation solution with a yield based on ACH of <5%. At more or less complete ACH conversion, this amidation which is quite selective per se proceeds with a yield (=sum of the intermediates described) of approx. 96-97%.

However, by-products formed in not inconsiderable amounts in this step are carbon monoxide, acetone, sulphonation products of acetone and cyclocondensation products of acetone with various intermediates.

The aim of the conversion is a substantially complete reaction of SIBAm and HIBAm to give MAA which proceeds under β-elimination of sulphuric acid (in excess sulphuric acid as the solvent).

In the process step of conversion, the sulphuric acid (anhydrous) solution of HIBAm, SIBAm and MAA (each present as hydrogensulphates) is reacted in the conversion at high temperatures between 140° C.-160° C. and short residence times of about 10 min or less.

The conversion mixture of this procedure is characterized by a high excess of sulphuric acid and the presence of the main product MAA·$H_2SO_4$ with a concentration in the solution of about 30-35% by weight (depending on the sulphuric acid excess used).

Depending on the water content in the sulphuric acid used, the proportion of HIBAm as well as SIBAm in the amidation mixture is also established. When, for example, 97% by weight sulphuric acid (1.5 equivalents of $H_2SO_4$ based on ACH) is used, about 25% by weight of HIBAm forms and can no longer be selectively and fully reacted in the conversion to give MAA. A relatively high water content in the amidation at temperatures of 90° C.-110° C. thus results in a relatively high proportion of HIBAm which can be converted by conventional conversion only relatively unselectively to the target intermediate MAA·$H_2SO_4$.

In the case of more or less complete SIBAm·$H_2SO_4$ reaction, the conversion step proceeds with an MAA·$H_2SO_4$ yield of approx. 94-95%. Adding the losses in the amidation as a result of the above-described side reactions, only between 90-92% MAA (based on ACH) is thus available for the subsequent esterification to the methyl methacrylate (MMA) desired as the product.

As a result of the drastic reaction conditions, by-products which are formed in this process step are considerable amounts of condensation and addition products of the intermediates with one another.

The aim of the esterification is the substantially complete reaction of MAA·$H_2SO_4$ from the conversion to MMA. The esterification proceeds by addition of a mixture consisting of water and methanol to the MAA-sulphuric acid solution and proceeds at least partly via methacrylic acid (MA) as an intermediate. The reaction may be operated under pressure or at ambient pressure.

Typically, hydrolysis/esterification of the conversion solution at temperatures between 90° C.-140° C. at reaction times of one or more hours provide a sulphuric acid solution of MMA, MA and ammonium hydrogensulphate which has formed.

The reaction conditions in the presence of free sulphuric acid result in the methanol selectivity in this step being only about 90% or less, and dimethyl ether is formed as a by-product by condensation of methanol.

In the case of more or less complete MAA·$H_2SO_4$ reaction, the esterification proceeds with an MMA yield of approx. 98-99% based on MAA used (total selectivity of MA+MMA). Adding the losses in the amidation and the conversion as a result of the above-described side reactions, it is thus possible in the overall process over all stages to achieve maximum MMA yields of 90% based on ACH in an optimal reaction.

In addition to the poor overall yields of the above-described process which, especially on the production scale, are associated with the occurrence of considerable amounts of wastes and offgases, this process has the disadvantage that massively superstoichometric amounts of sulphuric acid have to be used. From the ammonium hydrogen- and sulphuric acid-containing process acid which is regenerated in the sulphuric acid contact plant, tarlike, solid condensation products additionally separate out and prevent trouble-free conveying of the process acid and have to be removed at considerable cost and inconvenience.

As a consequence of the drastic yield losses in the above-described process of U.S. Pat. No. 4,529,816, there are some proposals to amidate and hydrolyse ACH in the presence of water, in which case the hydroxyl function in the molecular unit is retained at least in the first steps of the reaction.

These proposals for an alternative amidation in the presence of water lead, depending on whether they are carried out in the presence or without methanol, either to the formation of methyl hydroxyisobutyrate (=MHIB) or to the formation of 2-hydroxyisobutyric acid (=HIBAc).

Hydroxyisobutyric acid is a central intermediate for the preparation of methacrylic acid and methacrylic esters derived therefrom, especially methyl methacrylate, which, owing to their use as the monomers for the preparation of various polymers, have gained great industrial significance.

A further alternative for the preparation of esters of alpha-hydroxyisobutyric acid, especially methyl alpha-hydroxyisobutyrate, starting from ACH is described in JP Hei-4-193845. In JP Hei-4-193845, ACH is initially amidated below 60° C. with 0.8 to 1.25 equivalents of sulphuric acid in the presence of less than 0.8 equivalent of water and subsequently reacted at temperatures of greater than (>) 55° C. with more than 1.2 equivalents of alcohol, especially methanol, to give MHIB or corresponding esters. No reference is made here to the presence of viscosity-lowering media which are stable toward the reaction matrix.

The disadvantages and problems of this process are the industrial implementation as a result of extreme viscosity formation at the end of the reaction.

Some approaches to the utilization and conversion of MHIB (=methyl alpha-hydroxyisobutyrate) by dehydrating to give methyl methacrylate are described in the patent literature.

For example, in EP 0 429 800, MHIB or a mixture of MHIB and a corresponding alpha or beta-alkoxy ester is reacted in the gas phase, in the presence of methanol as a cofeed, over a heterogeneous catalyst consisting of a crystalline alumino-silicate and a mixed dopant composed of firstly an alkali metal element and secondly a noble metal. Even though conversion and selectivity of the catalyst are quite good at least at the start of the reaction, there is a quite drastic deactivation of the catalyst with increasing reaction time, which is associated with falling yields.

A similar approach is followed by EP 0 941 984, in which the gas phase dehydrogenation of MHIB is described as a substep of an MMA synthesis in the presence of a heterogeneous catalyst consisting of an alkali metal salt of phosphoric acid on $SiO_2$. However, this multistage process is complicated overall, entails elevated pressures and thus expensive equipment in substeps and only affords unsatisfactory yields.

In addition to the above-described studies on the dehydration of MHIB and related esters to the corresponding alpha-beta-unsaturated methacrylic acid compounds in the gas phase, there are also proposals to carry out the reaction in the liquid phase, for example in U.S. Pat. No. 3,487,101.

JP 184047/1985 also describes the dehydration of MHIB in the presence of highly concentrated sulphuric acid (90-100% by weight). Disadvantages in this case are the high input amounts of sulphuric acid and the inevitable occurrence of large amounts of aqueous sulphuric acid which are formed in the course of the reaction by the release of water from MHIB. Owing the amounts of waste acid, this process is not gaining any economic importance.

The preparation of MA starting from hydroxyisobutyric acid is described, for example, in U.S. Pat. No. 3,487,101, where the preparation of various methacrylic acid derivatives, especially methacrylic acid and methacrylic esters, starting from hydroxyisobutyric acid in the liquid phase, is characterized in that the reaction of HIBAc to give methacrylic acid is carried out in the presence of a dissolved basic catalyst at high temperatures between 180° C.-320° C. in the presence of high-boiling esters (e.g. dimethyl phthalate) and internal anhydrides (e.g. phthalic anhydride). According to the patent, MA selectivities of around 98% are achieved at HIBAc conversions of >90%. No information is given on the long-term stability of the liquid catalyst solution, especially the exhaustion of the anhydride used.

DE-A 1 191367 relates to the preparation of methacrylic acid starting from hydroxyisobutyric acid in the liquid phase, characterized in that the reaction of HIBAc to give methacrylic acid is carried out in the presence of polymerization inhibitors (for example copper powder) in the presence of a catalyst mixture consisting of metal halides and alkali metal halides at high temperatures between 180-220° C. According to the patent, MA selectivities of >99% are achieved at HIBAc conversions of >90%. The best results are achieved with catalyst mixtures of zinc bromide and lithium bromide. It is commonly known that the use of halide-containing catalysts at high temperatures places drastic requirements on the materials to be used, and these problems relating to the halogenated entrained by-products in the distillate also occur in downstream parts of the plant.

EP 0 487 853 describes the preparation of methacrylic acid starting from acetone cyanohydrin, characterized in that, in the first step, ACH is reacted with water at moderate temperatures in the presence of a heterogeneous hydrolysis catalyst and, in the second step, hydroxyisobutyramide is reacted with methyl formate or methanol/carbon monoxide to form formamide and methyl hydroxyisobutyrate, and, in the third step, MHIB is hydrolysed with water in the presence of a heterogeneous ion exchanger to give hydroxyisobutyric acid, and, in the fourth step, HIBAc is dehydrated by allowing it to react in the liquid phase at high temperatures in the presence of a soluble alkali metal salt. The methacrylic acid preparation from HIBAc is described at high conversions of around 99% with more or less quantitative selectivities. The multitude of reaction steps needed and the necessity of intermediately isolating individual intermediates, especially also the performance of individual process steps at elevated pressure, make the process complicated and thus ultimately uneconomic.

DE-A 1 768 253 describes a process for preparing methacrylic acid by dehydrating alpha-hydroxyisobutyric acid, characterized in that HIBAc is reacted in the liquid phase at a temperature of at least 160° C. in the presence of a dehydration catalyst which consists of a metal salt and alpha-hydroxyisobutyric acid. Particularly suitable in this case are the alkali metal and alkaline earth metal salts of HIBAc which are prepared in an HIBAc melt by reacting suitable metal salts in situ. According to the patent, MA yields of up to 95% from HIBAc are described, the feed of the continuous procedure consisting of HIBAc and approx. 1.5% by weight of the alkali metal salt of HIBAc.

RU 89631 relates to a process for preparing methacrylic acid starting from hydroxyisobutyric acid by elimination of water in the liquid phase, characterized in that the reaction is carried out in the absence of a catalyst with an aqueous solution of HIBAc (up to 62% by weight of HIBAc in water) under pressure at high temperatures of 200° C.-240° C.

It is also known that hydroxyisobutyric acid can be prepared starting from acetone cyanohydrin (ACH) by hydrolysing the nitrile function in the presence of mineral acids (see US 222989; J. Brit. Chem. Soc. (1930); Chem. Ber. 72 (1939), 800).

Representative of such a process is, for example, the Japanese patent publication Sho 63-61932, in which ACH is hydrolysed to hydroxyisobutyric acid in a two-stage process. In this process, ACH is initially reacted in the presence of 0.2-1.0 mol of water and 0.5-2 equivalents of sulphuric acid to form the corresponding amide salts. Even in this step, the use of small concentrations of water and sulphuric acid which are needed to obtain good yields, and short reaction times and small amounts of waste process acid, massive problems occur with the stirrability of the amidation mixture as a result of high viscosity of the reaction batches, especially toward the end of the reaction time.

When the molar amount of water is increased to ensure a low viscosity, the reaction slows drastically and side reactions occur, especially the fragmentation of ACH into the acetone and hydrocyanic acid reactants which react further under the reaction conditions to give subsequent products. According to the preliminary remarks of the Japanese patent publication SHO 63-61932, increasing the temperature does allow the viscosity of the reaction mixture to be controlled and the corresponding reaction batches to become stirrable as a result of the fall in viscosity, but here too the side reactions increase drastically even at moderate temperatures, which ultimately manifests itself in only moderate yields (see comparative examples).

When low temperatures of <50° C. which would ensure a selective reaction are employed, the increase toward the end of the reaction time in the concentration of the amide salts which are sparingly soluble under the reaction conditions results initially in the formation of a suspension which is difficult to stir and finally in the complete solidification of the reaction batch.

In the second step of the Japanese patent publication SHO 63-61932, water is added to the amidation solution and hydrolysis is effected at higher temperatures than the amidation temperature, in the course of which hydroxyisobutyric acid is formed from the amide salts formed by the amidation to release ammonium hydrogen-sulphate.

Essential for the economic viability of an industrial process is not only the selective preparation of the HIBAc target product in the reaction, but also the isolation from the reaction matrix or the removal of HIBAc from the remaining process acid.

In JP Sho 57-131736, method for isolating alpha-oxyisobutyric acid (=HIBAc), this problem is treated by treating the reaction solution which is obtained after the reaction between acetone cyanohydrin, sulphuric acid and water by hydrolytic cleavage and comprises alpha-hydroxyisobutyric acid and acidic ammonium hydrogensulphate with an extractant, which transfers the hydroxyisobutyric acid into the extractant and the acidic ammonium sulphate remains in the aqueous phase.

In this process, the free sulphuric acid remaining in the reaction medium is neutralized before the extraction by treating with an alkaline medium in order to increase the degree of extraction of HIBAc into the organic extraction phase. The necessary neutralization is associated with a considerable additional input of amine or mineral base and thus with considerable waste amounts of corresponding salts which cannot be disposed of in an ecologically and economically viable way.

The disadvantages of JP Sho 57-131736, process for preparing MMA via methacrylamide-hydrogensulphate (reaction sequence: amidation-conversion-hydrolytic esterification), can be summarized as follows:

a.) Use of high molar sulphuric acid excesses based on ACH (in the industrial process, approx. 1.5-2 equivalents of sulphuric acid per equivalent of ACH)

b.) High yield losses in the amidation step (approx. 3-4%) and in the conversion step (approx. 5-6%), which is ultimately manifested in a maximum methacrylamide sulphate yield of approx. 91%.

c.) Large waste streams in the form of aqueous sulphuric acid in which ammonium hydrogensulphate and organic byproducts are dissolved. Separation of undefined tar residues from this process waste acid which necessitate an aftertreatment or costly and inconvenient disposal.

The disadvantages of the JP Sho 57-131736 process for preparing MMA via hydroxyisobutyric acid as a central intermediate (reaction sequence: amidation-hydrolysis; HIBAc synthesis-MA synthesis-hydrolytic esterification) can be summarized as follows:

a.) although low molar sulphuric acid excesses based on ACH (only approx. 1.0 equivalent of sulphuric acid per equivalent of ACH) are used, there are massive problems with viscosity and stirrability of the amidation medium up to complete solidification of the reaction batches; the proposed dilution of the amidation with alcohols (methanol) or various esters leads to incomplete ACH conversion under the reaction conditions, drastic increase in the side reactions or to chemical decomposition of the diluents;

b.) high yield losses in the amidation step (approx. 5-6%) and complicated extraction with an organic solvent to form a water- and HIBAc-containing extractant phase which has to be worked up by distillation with high energy consumption to isolate HIBAc. About 2 kg of process acid waste are generated per kg of HIBAc and contain about 34% by weight of water as well as 66% by weight of ammonium hydrogensulphate (see Japanese publication SHO-57-131736, Example 4). The regeneration of a waste salt solution with high water contents in a sulphuric acid contact plant (=SC plant) is associated with considerable energy consumption which distinctly limits the capacity of such an SC plant.

It is common to all these processes that the isolation of HIBAc from the ammonium hydrogensulphate-containing aqueous reaction matrix is very costly and inconvenient. An excessively high water content in the HIBAc-containing extractant phase also causes entrainment of ammonium hydrogensulphate into the subsequent MA stage which can no longer be operated continuously on the industrial scale over an acceptable period. The high energy consumption in the regeneration of highly concentrated aqueous process acid and also extraction streams additionally make the proposed procedures uneconomic and they do not offer any real alternative to the established procedure which, although unselective, is appropriate to the purpose owing to the small number of simple process steps.

It is thus an object of this invention to find a process for preparing methacrylic acid and corresponding esters starting from cyanohydrin, in which a.) a viscosity suitable for industrial performance is ensured in the amidation mixture by selection of a suitable inert, readily removable solvent while simultaneously ensuring rapid, highly selective product formation, b.) high yields of hydroxyisobutyric acid and MA are achieved starting from ACH (>95%), c.) reaction times below 60 minutes for preparing amide sulphate intermediates (=amidation) and are achieved below 120 min for the hydrolysis (=HIBAc preparation from amide sulfates), d.) a reduction in the amounts of process acid waste is achieved by reacting ACH with more or less stoichiometric amounts of sulphuric acid, and e.) a reduction and simplification of the necessary process operations is achieved by connecting the reaction stage of HIBAc and MA.

It is a further object of the present invention, starting from acetone cyanohydrin, to prepare hydroxyisobutyric acid (HIBAc) and methacrylic acid (MA) in high selectivity and yield with minimum consumption of the sulphuric acid consumed in the amidation stage and to ensure a simple method for isolation both of HIBAc and of MA without complicated process operations without adding further assistants.

One aspect of this invention is a process for the selective, economically viable preparation of methacrylic acid and methacrylic esters starting from acetone cyanohydrin (ACH), wherein, in a first step, 2-hydroxy-2-methylpropionic acid (2-hydroxyisobutyric acid) is prepared by reacting ACH with sulphuric acid in the presence of water and a suitable polar solvent and is isolated and methacrylic acid is subsequently prepared by β-elimination of water starting from 2-hydroxy-2-methylpropionic acid. In a third, optional step, the thus obtained methacrylic acid may be reacted with various alcohols by processes known per se to give the corresponding methacrylic esters.

A further aspect of the present invention relates in particular to a process for the highly selective preparation of hydroxyisobutyric acid starting from acetone cyanohydrin via the reaction sequence of amidation and hydrolysis, wherein, starting from acetone cyanohydrin, 2-hydroxy-isobutyramide is passed through as an intermediate in the form of a salt of a sulphuric acid which is hydrolysed without isolation to the desired product 2-hydroxyisobutyric acid.

Starting from 2-hydroxyisobutyric acid, methacrylic acid can be prepared in high yield and high purity by water elimination (β-elimination) in the liquid phase in the presence of suitable metal catalysts.

The present invention allows the highly selective preparation of methacrylic acid in yields, not achievable hitherto, based on ACH of >97% while simultaneously drastically reducing the amount of sulphuric acid needed for the reaction.

The present invention is a process for preparing methacrylic acid, characterized in that a) acetone cyanohydrin is reacted at temperatures below 80° C. with a maximum of 1.5 equivalents of sulphuric acid in the presence of 0.05-1.0 equivalent of water in the presence of a polar solvent inert under the reaction conditions to form an efficiently stirrable solution of the corresponding amide sulphates in the inert solvent, b) after adding water, this solution, in the presence of or after preceding removal of the inert polar solvent, is converted to a solution consisting substantially of water, ammonium hydrogensulphate and alpha-hydroxyisobutyric acid, c) hydroxyisobutyric acid is removed from the aqueous ammonium hydrogensulphate solution by extraction with a suitable extractant, d) after removing the extractant, the alpha-hydroxyisobutyric acid obtained in high concentration, in the presence of a metal salt of the alpha-hydroxyisobutyric acid, is converted at temperatures between 160-300° C. in the liquid phase to a mixture obtained as a distillate and consisting substantially of methacrylic acid and water, and e) methacrylic acid is obtained distillatively in highly pure form from this mixture or the product mixture obtained under d) (MAA water) is used as an extractant for the isolation of the alpha-hydroxyisobutyric acid in step c) and the materials of value are subsequently distillatively separated from one another.

In one aspect of the invention, step f) may be carried out in addition to the above-described steps a) to e):

f) the mixture, obtained under step c), of methacrylic acid/water or pure methacrylic acid itself is reacted with an alcohol to obtain the ester desired as the product (=methacrylic ester) in a form desired for the application by known methods.

The process is characterized in the first step a) by the reaction of acetone cyanohydrin with sulphuric acid in the presence of water and a suitable inert solvent to prepare hydroxyisobutyramide and, in the second step b), by the hydrolysis of the amide formed in situ by reaction with water.

The process according to the invention is further characterized in that full conversions of greater than (>)99% are achieved at reaction times for the amidation of below 60 min, preferably below 45 min, preferably below 30 min, more preferably below 20 min, and at reaction times for the hydrolysis of below 120 min, preferably below 100 min, more preferably below 75 min.

In step a), according to the invention, temperatures below 80° C., preferably between 20° C. and 80° C., preferably below 70° C., more preferably below 60° C., are employed.

According to the invention, the sulphuric acid is used with a maximum of 1.5 equivalents (based on ACH), preferably between 0.5 and 1.5 equivalents, preferably 0.8 to 1.5 equivalents and more preferably between 0.9 and 1.1 equivalents.

According to the invention, water is used in step a) in an amount of 0.05 to 1.0 equivalent based on ACH, preferably 0.1 to 0.5 equivalent.

In the hydrolysis stage, process step b), according to the invention, water is used in an amount of 0.5 to 10 equivalents, based on ACH, preferably 1.0 to 6.5 equivalents, preferably 1.0 to 4 equivalents.

A further essential feature of the process according to the invention is the advantageous recycling or circulation of the inert solvent. The process according to the invention is further characterized by a highly selective reaction which reduces the occurrence of by-products of the process to a minimum, from which distinct economic advantages ultimately derive.

The inventive procedure of the reaction steps described succeeds in a simple manner in preparing hydroxyisobutyric acid (HIBAc) highly selectively based on the acetone cyanohydrin used as a reactant in yields of at least 95%, preferably greater than 95%, preferentially greater than 98% and more preferably up to 99.5%, and simultaneously considerably reducing the amounts of sulphuric acid in comparison to the prior art processes.

A further distinct advantage over processes practised hitherto which are explained in the prior art is short reaction times of the individual process stages which ensure space-time yields of greater than 95%.

The substantially smaller amounts of sulphuric acid compared to the existing processes distinctly deburdens a downstream sulphuric acid contact plant in which the ammonium sulphate-containing aqueous waste stream is treated to regenerate sulphuric acid. At a given capacity of the sulphuric acid contact plant, the consequence is a distinct increase in production of material of value (methacrylic acid and methacrylic acid derivatives, substantially methyl methacrylate).

The process acid formed by the process according to the invention may be regenerated in a simple manner in a sulphuric acid contact unit and recycled into the process.

Examples of inert, polar solvents which can be used as viscosity moderators for hydroxycarboxyamides and hydroxycarboxylic acids formed in situ are inert $C_2$-$C_{12}$ carboxylic acids, aliphatic sulphonic acids and esters derived therefrom or inert nitro compounds.

Inventive $C_2$-$C_{12}$ carboxylic acids are carboxylic acids selected from the group of acetic acid, propionic acid, methylpropanoic acid, butyric acid, isobutyric acid and corresponding homologous longer-chain aliphatically branched and unbranched carboxylic acids, and particular preference is given to acetic acid. In addition to the carboxylic acids described here, it is also possible to use the esters derived therefrom, for example the corresponding methyl, ethyl, propyl, isopropyl or higher esters having C-4 to C-10 carbon atoms. Examples mentioned here are acetate esters of the carboxylic acids listed here.

From the group of the esters, the preferred solvents or viscosity moderators which can be used in the amidation are the esters of alpha-hydroxyisobutyric acid, and particular preference is given to using methyl alpha-hydroxyisobutyrate as the solvent of the amidation, since it is also formed as an intermediate in the process and can therefore be recycled partly into the first stage (amidation).

Methacrylic acid itself or corresponding analogous and homologous compounds may also be used as inert, polar solvents or viscosity moderators from the group of the carboxylic acids.

Inventive aliphatic sulphonic acids are methanesulphonic acid, ethanesulphonic acid, propanesulphonic acid and corresponding homologous compounds having a hydrocarbon radical having C-3-C-12 carbon atoms which may optionally be substituted or branched. Inventive substituted, aliphatic sulphonic acids may be selected from the group of the haloalkanesulphonic acids, for example trifluoromethanesulphonic acid and higher homologous compounds thereof. In addition to these carboxylic acids described here, it is also possible to use the esters derived therefrom, for example the corresponding methyl, ethyl, propyl, isopropyl or higher esters having C-4 to C-10 carbon atoms. Examples mentioned here include the methyl esters of the sulphonic acids listed here, especially methyl methanesulphonate.

Inventive inert nitro compounds are nitromethane, nitroethane, nitropropane and corresponding structurally isomeric compounds and mixtures of these nitro compounds.

Suitable extractants for the process according to the invention are in principle all substance classes listed as viscosity moderators/solvents, such as nitro compounds, sulphonic acids and esters derived therefrom, carboxylic acids and esters derived therefrom, methyl hydroxyisobutyrate, and also sparingly water-soluble ketones, ethers and aromatic solvents, especially methyl ketones of the general formula R—C═O—R' (where R=Me–and R'=C-1 to C-12 hydrocarbons) which may be branched or unbranched. Particular preference is given to methyl ethyl ketone and methyl isobutyl ketone. Symmetric and unsymmetric ketones may also be used in accordance with the invention as solvents, for example diethyl ketone. Inventive aromatic extracts are, for example, benzene, toluene and xylene.

Metal salts which can be used as a catalyst of the dehydrogenation of HIBAc to MA are alkali metal and alkaline earth metal salts which form the corresponding metal-hydroxyisobutyrate salt in solution with the HIBAc reactant. Preference is given to the alkali metal and alkaline earth metal hydroxides or oxides, carbonates and hydrogencarbonates. Particular preference is given to the hydroxide, oxide and corresponding carbonates and hydrogencarbonates of lithium, sodium, potassium and magnesium, calcium and barium.

Examples of the alcohols which can be used in accordance with the invention in process step f) are $C_1$ to $C_{12}$ alcohols, especially methanol, ethanol, propanol and corresponding homologous and analogous compounds up to $C_{12}$ hydrocarbons.

Overall, the process according to the invention proceeds over the following process stages:

a.) Amidation:
Preparation of a solution consisting substantially of the hydrogensulphate salt of alpha-hydroxyisobutyramide, the monosulphuric ester of alpha-hydroxyisobutyramide and a viscosity moderator/solvent by reacting acetone cyanohydrin with sulphuric acid in the presence of water and the viscosity moderator/solvent;

b.) Hydrolysis:
Preparation of an aqueous solution of alpha-hydroxyisobutyric acid and ammonium hydrogen-sulphate by reacting the solution, prepared under a.), of the amide with water, optionally in the presence of the solvent described under a.);

c.) Circulation of the solvent: Removal of the inert solvent used under a.) before or after hydrolysis (step b.) and recycling of the solvent/viscosity moderator into process stage a.);

d.) Isolation of HIBAc:
Removal of the HIBAc desired as a product from the process acid by extraction from the aqueous, ammonium hydrogensulphate-containing HIBAc solution obtained after process steps b.) and c.) with a suitable organic solvent and subsequent isolation of HIBAc by removal of the extractant or by crystallization; and e.) β-elimination:
Preparation of methacrylic acid by reacting the alpha-hydroxyisobutyric acid obtained under e.) in the liquid phase in the presence of a metal salt of alpha-hydroxyisobutyric acid with elimination of water (β-elimination of water).

FIG. 1 shows a schematic overview of the essential chemical reactions of the process according to the invention with nitromethane as an exemplary solvent of the amidation.

The present invention is illustrated in detail herein-below with reference to working examples.

COMPARATIVE EXAMPLE A

Some examples from JP Hei-4-193845 were reproduced. It was found that when virtually stoichiometric amounts of sulphuric acid and water contents of approx. 0.1 equivalent are used as specified (see Examples 1-8 in the patent), the viscosity can no longer be controlled towards the end of the reaction even at the maximum reaction temperature, the entire batch solidifies and the mechanical stirrer used breaks. As a remedy, in the course of the reaction or even on commencement of the ACH metering, operation was effected in the presence of methanol or of methyl hydroxyisobutyrate, thus ensuring sufficient viscosity of the amidation mixture.

With variation of the parameters within the limits specified, it was found that, although the viscosity of the amidation mixture is sufficiently low (i.e. stirrability of the reaction batch can be ensured) under these conditions, the ACH conversion is no longer complete (in the case of the use of methanol), or else the ester added as a solvent (in the case of the use of MHIB as the solvent) decomposes under the reaction conditions.

Although the process is good with regard to the achievable ester yields, the necessary reaction times (with an amidation time of 2 hours and an esterification time of 6 hours to obtain good yields) make the process extremely uneconomic.

EXAMPLE 1

Preparation of Hydroxyisobutyric Acid in the Presence of Nitromethane 58.9 g of 91.6% by weight $H_2SO_4$ (100% by weight contains 53.95 g of 550 mmol or sulphuric acid) are admixed with 30 g of nitromethane (techn.) with stirring and without stabilizer. The colourless solution thus contains 4.95 g of water (=0.275 mol). This solution is initially charged in a 250 ml three-necked flask at 40° C. By means of an HPLC pump, 0.5 mol of ACH (=42.6 g) with a conveying rate of 2.3 ml/min is added with mechanical stirring to this "aqueous" sulphuric acid, in the course of which the distinct exothermicity during the reaction is captured with a water bath (i.e. reaction temperature: 40° C.). During the first part of the ACH addition (0-15 min ACH addition), the operating temperature is 40° C.; in the course of this, the reaction solution is clear and has very low viscosity.

During the second part of the ACH addition (i.e. from the 15th minute to minute 20 of the ACH addition), the operating temperature is 45° C.; in the course of this, the reaction solution is clear and somewhat more viscous, but very efficiently stirrable. The gas evolution is minimal in comparison to all other procedures; the stirrability over the entire amidation time is very good.

The total metering time is precisely 20 min; this is followed by a post-reaction time of 10 mm at 55° C. The molar ACH/sulphuric acid/water ratio is thus 1:1.1:0.55.

A yield of 131.3 g (theory —131.5 g) is obtained, which corresponds to quantitative recovery. Only minimal gas evolution is observed. After the amidation has ended, 85.05 g of water are added rapidly with cooling (temperature about 50° C.-60° C.) to the viscous reaction solution. This corresponds to a stoichiometry of HIBAm/sulphuric acid/water of 1:1.1:10.

This solution is heated to 120° C. in an oil bath in the Schott bottle (under moderate pressure, approx. 2.5 $bar_{abs}$.) for 1 h, in the course of which HIBAm is converted completely to HIBAc. At the end of the reaction, a colourless solution of 213.9 g which can be stirred readily (water-clear solution of very low viscosity) and which, according to HPLC, contains 23.7% by weight of hydroxyisobutyric acid (50.7 g=0.487 mol of HIBAc=98.0% of theory based on ACH) is obtained. As a further by-product to be determined by HPLC, acetone is found (0.16% by weight, i.e. approx. 1.0% of theory based on ACH).

In the simplest case, ACH may thus be reacted with a slight excess of aqueous sulphuric acid (in the presence of nitromethane as a viscosity moderator of the amidation) at moderate temperatures (40° C.-55° C.) initially to give an HIBAm.$H_2SO_4$/$H_2SO_4$ mixture which is selectively hydrolysed to HIBAc in the second step by reaction with water.

Nitromethane may be removed after the hydrolysis by removal of the azeotrope with water and recycled into the amidation.

EXAMPLE 2

Preparation of Hydroxyisobutyric Acid in the Presence of Acetic Acid 56.5 g of 95.55% by weight $H_2SO_4$ (100% by weight contains 53.95 g or 550 mmol) are admixed with stirring with 100 mg of hydroquinone which goes slowly into solution. The colourless solution thus contains 2.55 g of water (=0.142 mol). This solution is initially charged at 40° C. in a 250 ml three-necked flask. By means of an HPLC pump, 0.5 mol of ACH (=42.6 g) is added with mechanical stirring to this "aqueous" sulphuric acid with a conveying rate of 2.3 ml/min, in the course of which the distinct exothermicity is captured with a water-bath during the reaction (i.e. reaction temperature: 40° C.-45° C.). During the first half of the ACH addition (i.e. 0-10 min of ACH addition), the reaction solution is clear and of a honey-like consistency; after about 10 min, first, finely distributed gas bubbles then occur which can be attributed to ACH fragmentation to CO.

After 10 minutes, 30 g of acetic acid are added to the reaction solution through a separate dropping funnel over 4-8 minutes, in the course of which the ACH metering is continued.

The total metering time is precisely 20 min, and this followed by a post-reaction time of 40 min at 55° C. The molar ACH/sulphuric acid/water ratio is thus 1:1.1:0.28.

A yield of 129.1 g is obtained (theory=129.1 g), which corresponds to quantitative recovery. Only minimal gas evolution is observed. After the amidation has ended, 87.5 g of water are added rapidly with cooling (temperature about 50° C.-60° C.) to the viscous reaction solution. This corresponds to a stoichiometry of HIBAm/sulphuric acid/water of 1:1.1:10.

This solution is heated to 130° C. in an oil bath in the Schott bottle (under moderate pressure) for 1 h, in the course of which HIBAm is converted completely to HIBAc. After 30 min and 60 min, a sample is in each case taken in order to monitor the progress of the reaction.

At the end of the reaction, a colourless solution of 214.7 g is obtained which can be stirred readily (water-clear solution of very low viscosity) which, according to HPLC, already 23.95% by weight of hydroxyisobutyric acid (51.42 g=0.493 mol of HIBAc=98.8% of theory based on ACH) after 30 min. After 1 h, 23.90% by weight of HIBAc are still detected. As the only by-product to be detected, acetone is found (0.15% by weight, i.e. approx. 1% of theory based on ACH).

In the simplest case, ACH may thus be reacted with a slight excess of aqueous sulphuric acid (in the presence of acetic acid as a viscosity moderator of the amidation) at moderate temperatures (40° C.-60° C.) initially to give an HIBAm.$H_2SO_4$/$H_2SO_4$ mixture which is hydrolysed selectively to give HIBAc in the second step by reaction with water.

EXAMPLE 3

Preparation of Methyl Hydroxyisobutyrate in the Presence of Acetic Acid 53.5 g of 96.2% by weight $H_2SO_4$ (100% by weight contains 51.5 g or 525 mmol) are initially charged without hydroquinones. The colourless solution thus contains 2.0 g of water (=0.11 mol or 22 mol % based on ACH). With stirring and capture of slight exothermicity, 30 g of acetic acid are added to this (=0.5 mol). This solution is initially charged at 40° C. in a 250 ml three-necked flask. By means of a dropping funnel, with addition of 0.5 mol of ACH (=42.6 g) are added with a conveying rate of approx. 2.3 ml/min to this "aqueous"

sulphuric acid-AcOH solution, in the course of which the distinct exothermicity during the reaction is captured with a water-bath (i.e. reaction temperature: 45° C.-50° C.). During the first half of the ACH addition (i.e. 0-10 min of ACH addition), the reaction solution is clear and readily stirrable; after about 10 min, a few first, finely distributed gas bubbles then occur which can be attributed to ACH fragmentation to CO.

The total metering time is precisely 20 min; this is followed by a post-reaction time of 40 min at 55° C. The molar ACH/sulphuric acid/water ratio is thus 1:1.05:0.22.

A yield of 126.2 g (theory=126.1 g) is obtained, which corresponds to a quantitative recovery. Only minimal gas evolution is observed. After the amidation has ended, 11.5 g of water and 4 equivalents of methanol (64 g of MeOH) are added rapidly to the viscous reaction solution with cooling (temperature about 50° C.). This corresponds to a stoichiometry of HIBAm/sulphuric acid/water/MeOH of 1:1.05:1.5:4.

This solution is heated to 115° C. in an oil bath in the Schott bottle (under moderate pressure) for 1 h, in the course of which HIBAm is converted completely to HIBAc-MHIB. After 60 min, a sample is taken in each case in order to monitor the progress of the reaction.

At the end of the reaction, a colourless biphasic solution of 201.8 g which can be stirred readily is obtained (water-clear solution of very low viscosity), and is made up to a total of 400 g with water to thus obtain a monophasic solution which, according to HPLC, contains 2.5% by weight of hydroxyisobutyric acid (10.0 g=0.0962 mol of HIBAc=19.2% of theory based on ACH) after 60 min; in addition, 12.0% by weight of MHIB (=48.0 g=0.40 mol=81.5%) are also detected. As the single product, according to the HPLC method, methyl acetate is detected (7.4% by weight, i.e. 29.6 g=0.40 mol of MeAc, i.e. 80% based on acetic acid).

The total yield of HIBAc+MHIB in this reaction is thus 100.7% based on ACH (is thus quantitative).

In the simplest case, ACH can thus be reacted with a slight excess of aqueous sulphuric acid (in the presence of acetic acid as a viscosity moderator of the amidation) at moderate temperatures (40° C.-60° C.) initially to give an HIBAm.$H_2SO_4$/$H_2SO_4$ mixture which is hydrolysed/esterified selectively in the second step by reaction with water/methanol to give a mixture of HIBAc and MHIB (ratio approx. 1:4).

The biphasicity of the solution obtained after the reaction results from the presence of methyl acetate which separates impeccably from the salt solution and simultaneously extracts MHIB.

EXAMPLE 4

Preparation of Hydroxyisobutyric Acid in the Presence of Methanesulphonic Acid 56.5 g of 95.55% by weight $H_2SO_4$ (100% by weight contains 53.95 g or 550 mmol) are initially charged with stirring without hydroquinone. The colourless solution thus contains 2.55 g of water (=0.142 mol). This solution is placed in a 250 ml three-necked flask at 40° C. 30 g of methanesulphonic acid are added as viscosity moderator to this solution and can be added dropwise without noticeable exothermicity.

By means of an HPLC pump, 0.5 mol of ACH (=42.6 g) is added with a conveying rate of 2.3 ml/min to this "aqueous" sulphuric acid/methanesulphonic acid solution with mechanical stirring, in the course of which the distinct exothermicity during the reaction is captured with a water bath (i.e. reaction temperature: 40° C.-45° C.). During the first half of the ACH addition (i.e. 0-10 min of the ACH addition), the reaction solution is clear and of a consistency like honey; after about 10 min, the first, finely distributed gas bubbles occur which can be attributed to very slight ACH fragmentation to CO.

The total metering time is precisely 20 min; this is followed by a post-reaction time of 40 min at 55° C. The molar ACH/sulphuric acid/water ratio is thus 1:1.1:0.28.

A yield of 129.1 g (theory=129.1 g) is obtained, which corresponds to quantitative recovery. Only minimal gas evolution is observed. After the amidation has ended, 87.5 g of water are added rapidly to the viscous reaction solution with cooling (temperature about 50° C.-60° C.). This corresponds to a stoichiometry of HIBAm/sulphuric acid/water of 1:1.1:10.

This solution is heated to 130° C. in an oil bath in the Schott bottle (under moderate pressure) for 1 h, in the course of which HIBAm is converted completely to HIBAc.

After 30 min and 60 min, a sample is in each case taken in order to monitor the progress of the reaction.

At the end of the reaction, a colourless solution of 215.2 g is obtained which can be stirred readily (water-clear solution of very low viscosity) which, according to HPLC, already contains 24.0% by weight of hydroxyisobutyric acid (51.7 g=0.497 mol of HIBAc=99.3% of theory based on ACH) after 60 min. As the only by-product to be detected, acetone is found (0.3% by weight, i.e. 0.65 g or 1.1 mmol or 0.3% of theory based on ACH).

In the simplest case, ACH can thus be reacted with a slight excess of aqueous sulphuric acid (in the presence of methanesulphonic acid (MS) as a viscosity moderator of the amidation) at moderate temperatures (40° C.-60° C.) initially to give an HIBAm-$H_2SO_4$/$H_2SO_4$ mixture which is hydrolysed selectively to HIBAc in the second step by reacting with water.

The results of Examples 1 and 2 are compiled in Table 1:

TABLE 1

| Example No. | $H_2SO_4$ conc. (% by wt.) | Molar ACH-$H_2O$—$H_2SO_4$ ratio in amidation | Amidation reaction temp./time [° C.]/min | Molar ACH-$H_2O$—$H_2SO_4$-Sol* ratio in hydrolysis | Hydrolysis reaction temp./time [° C.]/min | ACH conversion | HIBAc/MHIB yield |
|---|---|---|---|---|---|---|---|
| 1 | 91.6 | 1/0.55/1.1 + 60 g of nitromethane | 40-55° C./30 min (15 min at 40° C., 5 min at 55° C., post-reaction 10 min at 55° C. | 1/10/1.1 + 60 g of nitromethane | 120° C./60 min | >99% | 98.0% HIBAc 1.2% acetone |

TABLE 1-continued

| Example No. | $H_2SO_4$ conc. (% by wt.) | Molar ACH-$H_2O$—$H_2SO_4$ ratio in amidation | Amidation reaction temp./time [° C.]/min | Molar ACH-$H_2O$—$H_2SO_4$-Sol* ratio in hydrolysis | Hydrolysis reaction temp./time [° C.]/min | ACH conversion | HIBAc/MHIB yield |
|---|---|---|---|---|---|---|---|
| 2 | 95.6 | 1/0.3/1.1 + 1.0 mol of acetic acid | Stage 1: 10 min at 40° C., Stage 2: 10 min at 55° C., post-reaction: 40 min 55° C. | 1/10/1.1/1.0 of acetic acid | 130° C./30 min | >99% | 98.8 HIBAc 1.0% acetone no MMA |

*Sol = solvent

EXAMPLES 5-10

Preparation of Hydroxyisobutyric Acid from ACH in the Presence of Nitromethane with Different Water Contents and Hydrolysis Parameters The standard mixture consisted of aqueous sulphuric acid and nitromethane, mixed and initially charged in a three-necked flask at approx. 35° C., to which were subsequently metered with cooling 0.5 mol of ACH at 2.3 ml/min by HPLC pump (unless stated otherwise), and the mixture was subsequently post-reacted in accordance with the table entry. Subsequently, water was added and hydrolysis was effected in the Schott bottle without stirring. Yield determination after hydrolysis with water by HPLC quantification (against external standard) of HIBAc and acetone in the crude solution. The results of these Examples 5-10 are shown in Table 2.

EXAMPLES 11-18

Preparation of Hydroxyisobutyric Acid from ACH in the Presence of Various Viscosity Moderators The standard batch consisted of aqueous sulphuric acid and nitromethane, mixed and initially charged in a three-necked flask at approx. 35° C., to which was metered with cooling 0.5 mol of ACH at 2.3 ml/min by HPLC pump (unless stated otherwise), followed by post-reaction according to the table entry. Subsequently, water was added and hydrolysis was effected without stirring in the Schott bottle; yield determination after hydrolysis with water by HPLC quantification (against external standard) of HIBAc and acetone in the crude solution. The viscosity moderators were selected from the group of nitroalkanes, sulphonic esters, methyl hydroxyisobutyrates and carboxylic acids (isobutyric acid as an example). The results of these Examples 11-18 are summarized in Table 3:

TABLE 2

| Example No. | $H_2SO_4$ conc. (% by wt.) | Molar ACH-$H_2O$—$H_2SO_4$ ratio in amidation | Amidation reaction temp./time [° C.]/min | Molar ACH-$H_2O$—$H_2SO_4$-Sol* ratio in hydrolysis | Hydrolysis reaction temp./time [° C.]/min | ACH conversion | HIBAc yield |
|---|---|---|---|---|---|---|---|
| 5 | 91.6% | 1/0.6/1.1 + 60 g of nitromethane | 40-55° C./30 min (15 min at 40° C., 5 min at 55° C., post-reaction 10 min at 55° C.) | 1/10/1.1 + 60 g of nitromethane | 120° C./60 min | >99% | 98.0% HIBAc 1.2% acetone |
| 6 | 93.0% | 1/0.45/1.1 + 100 g of nitromethane | 40-55° C./30 min (15 min at 40° C., 5 min at 55° C., 10 min at 55° C.) | 1/10/1.1 + 60 g of nitromethane | 120° C./60 min | >99% | 99.2% HIBAc 0.8% acetone |
| 7 | 91.5% | 1/0.53/1.05 + 60 g of nitromethane | 40-50° C./30 min (15 min at 45° C., 5 min at 50° C., 10 min at 60° C.) | 1/6/1.05 + 60 g of nitromethane | 120° C./60 min | >99% | 98.4% HIBAc n.d.** % acetone |
| 8 | 92.9% | 1/0.42/1.0 + 60 g of nitromethane | 40-55° C./30 min (15 min at 40° C., 5 min at 55° C., 10 min at 55° C.) | 1/6/1.0 + 60 g of nitromethane | 120° C./60 min | >99% | 98.7% HIBAc 1.2% acetone |
| 9 | 92.9% | 1/0.42/1.0 + 60 g of nitromethane | 40-55° C./30 min (15 min at 40° C., 5 min at 55° C., 10 min at 55° C.) | 1/10/1.0 + 60 g of nitromethane | 120° C./60 min | >99% | 98.8% HIBAc 1.2% acetone |
| 10 | 92.9% | 1/0.43/1.05 + 60 g of nitromethane | 40-55° C./15 min (7.5 min at 43° C., 2.5 min at 55° C., 5 min at 55° C.) | 1/5/1.05 + 60 g of nitromethane | 130° C./30 min | >99% | 98.6% HIBAc 1.3% acetone |

*Sol = solvent
**n.d. = not determined

TABLE 3

| Example No. | H$_2$SO$_4$ conc. (% by wt.) | Molar ACH-H$_2$O—H$_2$SO$_4$ ratio in amidation | Amidation reaction temp./time [° C.]/min | Molar ACH-H$_2$O—H$_2$SO$_4$-Sol* ratio in hydrolysis | Hydrolysis reaction temp./time [° C.]/min | ACH conversion | HIBAc yield |
|---|---|---|---|---|---|---|---|
| 11 | 91.6% | 1/0.6/1.1 + 60 g of nitroethane | 40-55° C./20 min (10 min at 40° C., 5 min at 55° C., post-reaction 5 min at 55° C.) | 1/10/1.1 (contains 60 g of nitroethane) | 120° C./45 min | >99% | 99.0% HIBAc 0.8% acetone |
| 12 | 93.0% | 1/0.45/1.1 + 100 g of nitropropane | 40-55° C./30 min (15 min at 40° C., 5 min at 55° C., 10 min at 55° C.) | 1/10/1.1 (contains 100 g of nitropropane) | 130° C./60 min | >99% | 99.2% HIBAc 0.8% acetone |
| 13 | 91.5% | 1/0.53/1.05 + 60 g of nitroethane | 40-50° C./20 min (10 min at 45° C., 5 min at 50° C., 10 min at 60° C.) | 1/6/1.05 + 60 g of nitroethane | 130° C./60 min | >99% | 98.0% HIBAc 1.4% acetone |
| 14 | 92.9% | 1.0/0.42/1.0 + 30 g of nitromethane | 40-55° C./30 min (15 min at 40° C., 5 min at 55° C., 10 min at 55° C.) | 1/6/1.0 + 60 g of nitromethane | 120° C./60 min | >99% | 98.9% HIBAc 1.0% acetone |
| 15 | 92.9% | 1/0.38/0.9 + 30 g of nitromethane | 40-55° C./30 min (15 min at 40° C., 5 min at 55° C., 10 min at 55° C.) | 1/10/0.9 (contains 30 g of nitromethane) | 120° C./60 min | >99% | 97.9% HIBAc 1.9% acetone |
| 16 | 92.9% | 1/0.38/0.9 + 30 g of nitromethane | 40-55° C./15 min (10 min at 40° C., 10 min at 55° C., 5 min at 55° C.) | 1/6/0.9 (contains 30 g of nitromethane) | 130° C./60 min | >99% | 98.0% HIBAc 1.7% acetone |
| 17 | 93.1% | 1/0.41/1.0 + 30 g of nitromethane | 40-55° C./20 min (10 min at 40° C., 5 min at 55° C.) | 1/7.1/1.0 (contains 30 g of nitromethane) | 130° C./30 min | >99% | 99.0% HIBAc 0.5% acetone |
| 18 | 93.1% | 1/0.41/1.0 + 50 g of methyl methanesulphonate | 40-55° C./20 min (10 min at 40° C., 5 min at 55° C.) | 1/6.0/1.0 (contains 50 g of sulphonic ester) | 130° C./60 min | >99% | 98.0% HIBAc 1.1% acetone |

*Sol = solvent

The invention claimed is:

1. A process for preparing methacrylic acid comprising:
   a) reacting acetone cyanohydrin with a maximum of 1.2 equivalents of sulphuric acid in the presence of 0.05-1.0 equivalent of water; wherein said reacting occurs in the presence of an inert polar solvent at a temperature below 80° C. and forms a stirrable solution of the corresponding amide sulphate(s) in the inert solvent,
   b) adding water to the stirrable solution of a) and removing the inert polar solvent to produce a solution containing water, ammonium hydrogensulphate and alpha-hydroxyisobutyric acid,
   c) adding an extractant to remove the hydroxyisobutyric acid from the solution produced by b) and recovering a solution containing alpha-hydroxyisobutyric acid in the presence of a metal salt of alpha-hydroxyisobutyric acid
   d) converting in liquid phase the solution containing alpha-hydroxyisobutyric acid obtained by c) at a temperature between 160-300° C. to a mixture substantially comprising methacrylic acid and water, and
   e) recovering the methacrylic acid.

2. The process of claim 1, wherein process step a) is performed at a temperature of less than 70° C.

3. The process of claim 1, wherein the inert polar solvent is an inert $C_2$-$C_{12}$ carboxylic acid, inert nitro compound, or an aliphatic sulphonic acid.

4. The process of claim 1, wherein the inert polar solvent is a carboxylic acid selected from the group of acetic acid, propionic acid, methylpropanoic acid, butyric acid, and isobutyric acid; or a corresponding homologous longer-chain aliphatically branched or unbranched carboxylic acid.

5. The process of claim 1, wherein the inert polar solvent is acetic acid.

6. The process of claim 1, wherein the inert polar solvent is nitromethane.

7. The process of claim 1, wherein the inert polar solvent is methanesulphonic acid.

8. The process of claim 1, wherein the aqueous ammonium hydrogensulfate in the solution formed in step b) is removed by treatment in a sulphuric acid contact plant to form nitrogen and sulfuric acid, and the sulfuric acid is recycled into step a).

9. The process of claim 1, wherein the extractant in step c) is selected from the group consisting of nitro compounds, sulphonic acids and esters derived therefrom, carboxylic acids and esters derived therefrom, methyl hydroxyisobutyrate, and sparingly water-soluble ketones, ethers or aromatic solvents of the general formula R—C=O—R' (where R=Me- and R' is a $C_{-1}$ to $C_{-12}$ hydrocarbon group which may be branched or unbranched).

10. The process of claim 8, wherein said extract is methyl ethyl ketone or methyl isobutyl ketone.

11. The process of claim 1, further comprising step f):
   f) reacting the methacrylic acid with an alcohol to obtain a methacrylic acid ester.

12. The process of claim 11, wherein the alcohol is selected from the group consisting of methanol, ethanol, propanol and other $C_1$ to $C_{12}$ alcohols.

13. The process of claim 8, wherein a full conversion of greater than (>)99% is achieved at a reaction time for amidation in step a) of below 60 min and at a reaction time for hydrolysis in step d) of below 120 min.

14. The process of claim 8, wherein a full conversion of greater than (>)99% is achieved at a reaction time for amidation in step a) of below 30 min and at a reaction time for hydrolysis in step d) of below 100 min.

15. The process of claim 8, wherein a full conversion of greater than (>)99% is achieved at a reaction time for amidation in step a) of below 20 min and at a reaction time for hydrolysis in step d of below 75 min.

16. The process of claim 1, wherein the yield of methacrylic acid is at least 95%.

17. The process of claim 1, wherein the yield of methacrylic acid is at least 98%.

18. The process of claim 1, wherein the yield of methacrylic acid is at least 99.5%.

* * * * *